United States Patent
Futatsuyama et al.

(10) Patent No.: US 8,870,782 B2
(45) Date of Patent: Oct. 28, 2014

(54) PULSE WAVE ANALYZER AND BLOOD PRESSURE ESTIMATOR USING THE SAME

(75) Inventors: Kouki Futatsuyama, Anjo (JP);
Harutsugu Fukumoto, Anjo (JP);
Tsuyoshi Nakagawa, Aichi-ken (JP);
Naoki Mitsumoto, Nagoya (JP);
Tatsuya Ikegami, Nisshin (JP)

(73) Assignee: DENSO CORPORATION, Kariya (JP)

( * ) Notice: Subject to any disclaimer, the term of this patent is extended or adjusted under 35 U.S.C. 154(b) by 177 days.

(21) Appl. No.: 13/248,154

(22) Filed: Sep. 29, 2011

(65) Prior Publication Data

US 2012/0078123 A1   Mar. 29, 2012

(30) Foreign Application Priority Data

Sep. 29, 2010   (JP) ................. 2010-219408

(51) Int. Cl.
*A61B 5/026* (2006.01)
*A61B 5/021* (2006.01)
*A61B 5/00* (2006.01)
*A61B 5/0402* (2006.01)
*A61B 5/01* (2006.01)

(52) U.S. Cl.
CPC .......... *A61B 5/0402* (2013.01); *A61B 5/02125* (2013.01); *A61B 5/6893* (2013.01); *A61B 5/6843* (2013.01); *A61B 5/7239* (2013.01); *A61B 5/01* (2013.01)
USPC ........................................ 600/485; 600/500

(58) Field of Classification Search
USPC ................................. 600/485, 500
See application file for complete search history.

(56) References Cited

U.S. PATENT DOCUMENTS

| 4,911,167 | A | 3/1990 | Corenman et al. |
| 5,255,686 | A | 10/1993 | Takeda et al. |
| 6,027,453 | A | 2/2000 | Miwa et al. |
| 6,339,721 | B1 | 1/2002 | Yamazaki et al. |
| 6,645,155 | B2 * | 11/2003 | Inukai et al. .............. 600/485 |
| 7,534,212 | B2 | 5/2009 | Baker, Jr. |
| 7,945,313 | B2 | 5/2011 | Fuwamoto et al. |
| 2002/0177781 | A1 | 11/2002 | Amano |
| 2006/0025698 | A1 | 2/2006 | Nakagawa et al. |
| 2007/0066910 | A1 | 3/2007 | Inukai et al. |

FOREIGN PATENT DOCUMENTS

| JP | A-H02-045041 | 2/1990 |
| JP | A-H05-007558 | 1/1993 |
| JP | A-H05-312962 | 11/1993 |
| JP | A-H10-005186 | 1/1998 |

(Continued)

OTHER PUBLICATIONS

Office Action issued Oct. 9, 2012 in corresponding JP Application No. 2010-219408 (and English translation).

*Primary Examiner* — Carl H Layno
*Assistant Examiner* — Jon Eric C Morales
(74) *Attorney, Agent, or Firm* — Posz Law Group, PLC

(57) ABSTRACT

In a pulse wave analyzer, an ECG signal and a pulse wave signal are detected from an object to be analyzed. A plurality of feature points are extracting from the acquired ECG signal, the feature points appearing in a waveform of the ECG signal. The acquired pulse wave signal is segmented into a plurality of pulse wave signal pieces based on times at which the feature points appear. Each of the pulse wave signal pieces is segmented every heart beat. A reference pulse wave is calculated based on the plurality of pulse wave signal pieces, by multiplying the pulse wave signal pieces by coefficients and averaging the pulse wave signal pieces multiplied by the coefficients. The reference pulse wave is used to estimate the blood pressure of the object.

19 Claims, 10 Drawing Sheets

(56) References Cited

FOREIGN PATENT DOCUMENTS

| | | |
|---|---|---|
| JP | A-H10-295656 | 11/1998 |
| JP | A-H10-295657 | 11/1998 |
| JP | A-H10-314127 | 12/1998 |
| JP | A-H11-123181 | 5/1999 |
| JP | A-H11-276450 | 10/1999 |
| JP | A-H11-318837 | 11/1999 |
| JP | A-2000-126148 | 5/2000 |
| JP | A-2001-008907 | 1/2001 |
| JP | A-2002-153436 | 5/2002 |
| JP | A-2002-291713 | 10/2002 |
| JP | A-2003-000555 | 1/2003 |
| JP | A-2004-219338 | 8/2004 |
| JP | A-2005-245869 | 9/2005 |
| JP | A-2006-034803 | 2/2006 |
| JP | A-2006-263354 | 10/2006 |
| JP | A-2007-082682 | 4/2007 |
| JP | A-2007-144204 | 6/2007 |
| JP | B2-3965435 | 6/2007 |
| JP | A-2007-527770 | 10/2007 |
| JP | A-2007-301101 | 11/2007 |
| JP | A-2008-302127 | 12/2008 |
| JP | A-2009-022639 | 2/2009 |
| JP | A-2009-195571 | 9/2009 |

* cited by examiner

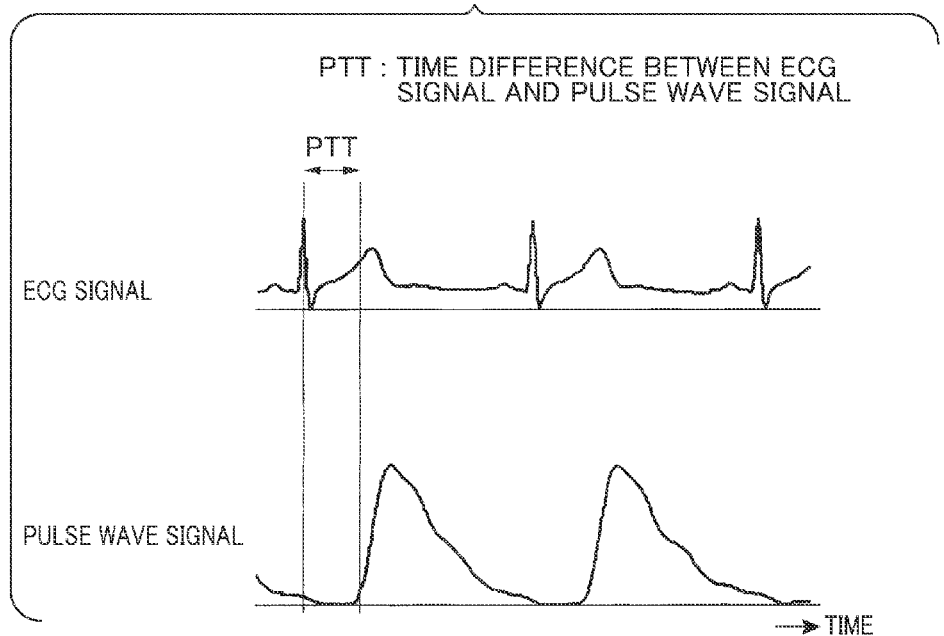
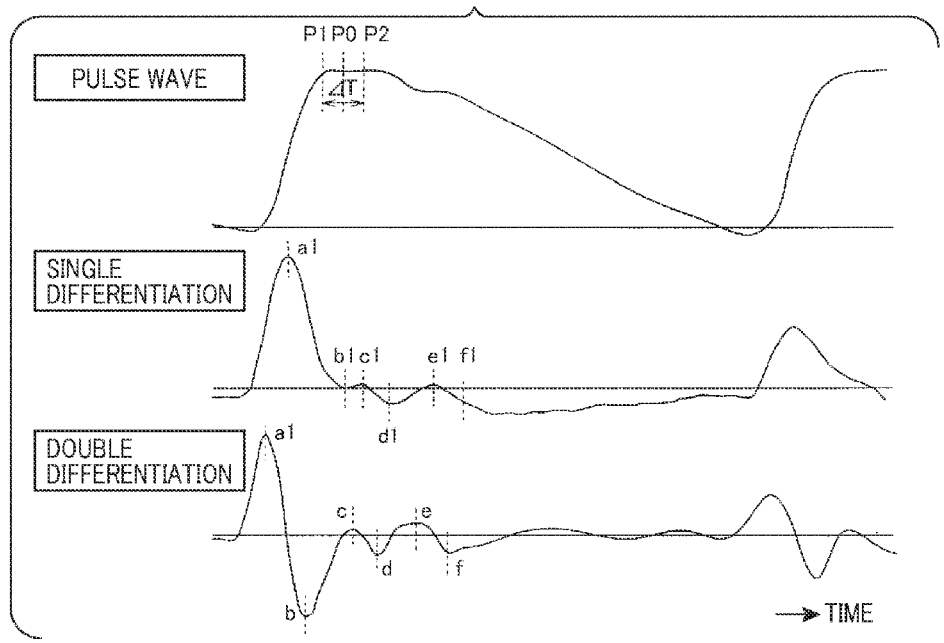

PULSE WAVE ANALYZER AND BLOOD PRESSURE ESTIMATOR USING THE SAME

CROSS-REFERENCE TO RELATED APPLICATION

This application is based on and claims the benefit of priority from earlier Japanese Patent Application No. 2010-219408 filed Sep. 29, 2010, the description of which is incorporated herein by reference.

BACKGROUND

1. Technical Field

The present invention relates to a pulse wave analyzer that analyzes pulse wave signals and a blood pressure estimating using the pulse wave analyzer.

2. Related Art

It is known that a cuff is used in general in measuring a blood pressure. However, use of a cuff raises a problem of giving feeling of pressure to the examinee due to the inflation of the cuff or a problem of disabling continuous measurement of blood pressure.

In this regard, recently, a different measurement technique is under development. In this measurement technique, pulse wave signals are analyzed to obtain a pulse wave velocity, feature points of pulse waves, and the like, for the calculation of a blood pressure (refer to JP-A-H10-295656, JP-A-H10-295657, JP-A-H11-318837, JP-A-2003-000555, JP-A-2001-008907, JP-A-2006-263354, JP-A-2007-082682 and JP-A-2008-302127). For example, volume pulse waves can be measured using light and thus the size of the device for the measurement can be reduced. In addition, use of measurement of volume pulse waves can eliminate the oppression given to the examinee and enables continuous measurement of blood pressure.

For example, in order to extract information from pulse wave signals, the waveforms are doubly differentiated. However, such a differentiation raises a problem of allowing the waveforms to be easily affected by disturbance. To take measures against this, pulse wave signals are averaged before being differentiated so that the pulse wave signals are cleaned (so that a high S/N ratio is obtained) (see JP-A-H05-312962 and JP-B-3965435).

In averaging pulse wave signals, the pulse wave signals are segmented and cut off on a beat-by-beat basis. To this end, base points of the segment are required to be determined. The techniques disclosed in JP-A-H05-312962 and JP-B-3965435 suggest use of differential peaks or double differential peaks of pulse wave signals as the base points for averaging. However, when large disturbance is caused, these peak positions cannot be detected with high accuracy. As a result, the accuracy in cut-off intervals of the pulse wave signals is lowered, and thus the effect of averaging is not well exerted, or the addition carried out in the averaging is likely to cause further disturbance in the waveforms of the pulse wave signals.

SUMMARY

The disclosure has been made in light of the problems set forth above. The disclosure provides a pulse wave analyzer which is able to appropriately perform averaging of pulse wave signals, and also provides a blood pressure estimator that uses the pulse wave analyzer.

As one aspect of the disclosure, there is provided a pulse wave analyzer comprising: signal acquiring means for acquiring an ECG (electrocardiographic) signal and a pulse wave signal which are detected from an object to be analyzed; feature point extracting means for extracting a plurality of feature points (or simply, features) from the acquired ECG signal, the feature points appearing in a waveform of the acquired ECG signal; signal segmenting means for segmenting the acquired pulse wave signal into a plurality of pulse wave signal pieces based on times (i.e., time instants) at which the plurality of feature points appear, each of the pulse wave signal pieces being segmented every heart beat; and calculating means for calculating a reference pulse wave based on the plurality of pulse wave signal pieces, by multiplying the plurality of pulse wave signal pieces by coefficients and averaging the plurality of pulse wave signal pieces multiplied by the coefficients.

In the pulse wave analyzer configured as set forth above, base points for segmenting the pulse wave signal are determined using feature points of ECG signals. Then, based on the base points, pulse wave signal pieces are cut off from the pulse wave signals. Comparing with pulse wave signals, ECG signals have definite feature points (e.g., peaks of waveforms). Accordingly, the feature points can be identified with high accuracy without performing differentiation. Thus, large noise influence is unlikely to be caused, which would have been caused if differentiation has been performed. In this way, pulse wave signal pieces are cut off on a beat-by-beat basis with high accuracy, leading to appropriate averaging of pulse waves and calculation of a reference pulse wave with high accuracy.

The "coefficient" here enables weighting of each of the pulse wave signal pieces when these signals are averaged. The coefficient may be set such that a separate pulse wave signal having higher reliability is more heavily weighted. Alternatively, the coefficient may be set to the same value (e.g., "1") for all the pulse wave signal pieces without performing weighting.

The "accuracy of cut-off" here refers to the degree of correctness in the uniformity (identicalness) of the waveforms of the cut-off pulse wave signal pieces. When the accuracy of cut-off is low, the peaks of the pulse waveforms (in particular, waveforms after differentiation) will be broadened (waveforms will be obtuse). Therefore, for example, feature points used for blood pressure estimation may no longer be detected. Also, the "accuracy of a reference pulse wave" refers to the degree of broadening in the peak of the waveform. Thus, higher accuracy of a reference pulse wave means that the peak is less broadened.

The base points may be determined based on the feature points of ECG signals. For example, times when feature points are extracted may be used as base points, or times deviated from the times of extraction of the feature points by a predetermined amount of time may be used as base points.

Any feature points may be used as the feature points of the waveforms of ECG signals. For example, the feature points are peaks of R-peaks of the waveform of the ECG signal.

R-peaks, each having a large height and a sharp peak, are easily detected and unlikely to cause errors. Thus, using R-peaks, base points for cutting off pulse wave signals can be appropriately determined.

It is preferred that the feature point extracting means includes a low-pass filter whose cutoff frequency is present in a range of 15 to 30 Hz and means for extracting the feature points from the waveform of the ECG signal processed by the low-pass filter.

When ECG signals are filtrated using a low-pass filter as mentioned above, the influence of high-frequency electromagnetic noise or noise caused by vibration or body motion is mitigated even when the noise is superposed on the ECG signals. Thus, the base points for cutting off pulse wave signals can be determined with good accuracy.

The ECG signals have a probability that the width of the peaks of the waveforms are broadened, being affected by the filtration. However, in the pulse wave analyzer of the disclosure, only the positions of feature points have to be detected and thus no inconveniences may be caused by the broadening.

Exact coincidence may not be achieved in the lengths (periods, or distances between base points) of respective pulse wave signal pieces delimited using the feature points of the waveforms of ECG signals. Accordingly, when a plurality of pulse wave signal pieces are averaged to calculate a reference pulse wave, the position of superposition is required to be determined in each of the pulse wave signal pieces. For example, each separate pulse wave signal may be superposed with reference to either a front or rear base point thereof, or with reference to the center between these base points.

It is also preferred that the calculating means is configured to calculate the reference pulse wave repeatedly at intervals with a part of the plurality of pulse wave signal pieces interchanged with another new pulse wave signal piece, wherein the calculating means is configured to adjust a position of the new pulse wave signal piece in a time axis such that both the new pulse wave signal piece and the reference pulse wave calculated immediately before the interchange have the largest coefficient of correlation therebetween.

The "position adjustment along a time axis" here refers to an adjustment, as shown in FIG. 9, in which the position of superposition of the separate pulse wave signal 45 with respect to the reference pulse wave 43 is shifted in the direction indicated by the arrow in the figure.

In the pulse wave analyzer configured as set forth above, a newest reference pulse wave can be consecutively acquired based on a newly acquired separate pulse wave signal. When a new separate pulse wave signal is acquired, the position of the new separate pulse wave signal along a time axis is adjusted to a position which can maximize the correlation coefficient between the new separate pulse wave signal and the already calculated reference pulse wave. Then, a new reference pulse wave is calculated using the positionally adjusted new separate pulse wave signal, with other pulse wave signal pieces being superposed thereon.

Thus, averaging is suppressed from being conducted at a position where the waveform of the positionally adjusted new separate pulse wave signal is deviated from those of other pulse wave signal pieces. Accordingly, the waveform of a reference pulse wave is suppressed from being broadened.

When the position is adjusted along a time axis, the position after adjustment may be indicated as a time parameter for shifting a position such as of either a front or rear base point of a separate pulse wave signal.

Specifically, when the correlation coefficient is maximized at a position delayed from a reference pulse wave by 5 msec, the position of the separate pulse wave signal may be stored as a parameter of "+5 msec". When pulse wave signal pieces are averaged, the parameter may be used to conduct position adjustment.

The pulse wave analyzer may have another configuration for adjusting position of a separate pulse wave signal along a time axis.

It is also preferred that the calculating means is configured to calculate the reference pulse wave repeatedly at intervals with a part of the plurality of pulse wave signal pieces interchanged with another new pulse wave signal piece, wherein the calculating means is configured to adjust a position of the new pulse wave signal piece in a time axis direction such that both the new pulse wave signal piece and the reference pulse wave calculated immediately before the interchange are averaged to produce a new pulse wave having a waveform having a predetermined peak which presents the largest sharpness degree.

When two pulse wave waveforms are averaged and if these waveforms are deviated along a time axis to a large extent, the waveform of the averaged pulse wave will be broadened and thus the sharpness degree of the peak will be lowered. On the other hand, if the deviation of the two waveforms is small, the sharpness degree of the waveform of the averaged pulse wave will be high.

Thus, in the pulse wave analyzer configured as set forth above, when a new separate pulse wave signal is acquired, the already calculated reference pulse wave and the new separate pulse wave signal are averaged to obtain a waveform of an averaged pulse wave. Then, the position of the new separate pulse wave is adjusted to a position where the sharpness degree of a predetermined peak in the obtained waveform is maximum, followed by calculating a reference pulse wave, with the new separate pulse wave being superposed on other pulse wave signal pieces.

Thus, the averaging of the newly acquired separate pulse wave signal and other pulse wave signal pieces is suppressed from being conducted at a position where the waveforms of the signals are deviated from each other. Accordingly, the waveform of the reference pulse wave is suppressed from being broadened.

Generally, pulse wave signals are differentiated in order to obtain peaks. The averaging of a separate pulse wave signal and a reference pulse wave as mentioned above may be conducted after the pulse waves are each differentiated. Alternatively, the pulse waves may be averaged prior to differentiation.

In the pulse wave analyzer of the disclosure, in calculating a reference pulse wave, pulse wave signal pieces are averaged, with a coefficient (weight coefficient) being added to each of the pulse wave signal pieces. The coefficient may be set to the same value for each of the pulse wave signal pieces. For example, as described above, a coefficient of "1" may be multiplied with each of all the pulse wave signal pieces. In this case, a coefficient is not required to be calculated for each of the pulse wave signal pieces and thus the processing load of the analyzer will be mitigated.

A coefficient may be set for the purpose of making a distinction between use and non-use of an acquired separate pulse wave signal for the calculation of a reference pulse wave. For example, the coefficient of each separate pulse wave signal may be either "0" or "1".

It is preferred that the pulse wave analyzer further comprises coefficient setting means for setting the coefficient based on parameters showing accuracy of measuring either the pulse signal or the ECG signal such that the higher the accuracy, the larger a contribution of the pulse wave signal pieces to the reference pulse wave.

With the pulse wave analyzer configured as set forth above, the separate pulse wave signal which is determined to have high measurement accuracy based on the parameter is ensured to greatly contribute to the calculation of a reference pulse wave. Contrarily, the separate pulse wave signal which is determined to have low measurement accuracy based on the parameter is ensured to have a small influence on a reference pulse wave. Thus, a reference pulse wave is calculated with high accuracy.

The "measurement accuracy" here refers to the degree of correctness in the measurement of pulse wave signals and ECG signals, or the degree of variation of pulse wave signals and ECG signals. Thus, "signals of high measurement accuracy" means that the signals are stable and have no noise and variation.

The pulse wave analyzer configured as set forth above is able to calculate a reference pulse wave of the driver or an occupant of the vehicle.

The blood pressure estimator configured as set forth above is able to estimate a blood pressure with high accuracy using the reference pulse wave calculated by the pulse wave analyzer.

BRIEF DESCRIPTION OF THE DRAWINGS

In the accompanying drawings:

FIG. 3 is a graph illustrating ECG signals and pulse wave signals;

FIG. 4 is a graph illustrating pulse wave signals and signals obtained by differentiating the pulse wave signals;

DETAILED DESCRIPTION OF THE PREFERRED EMBODIMENTS

With reference to the accompanying drawings, hereinafter are described some embodiments of the present invention.

First Embodiment

Referring to FIGS. 1 to 7, a first embodiment of the present invention is described. The first embodiment exemplifies a blood pressure estimation system which is installed in a vehicle (automobile) to measure blood pressure of the driver.

Figure 1:
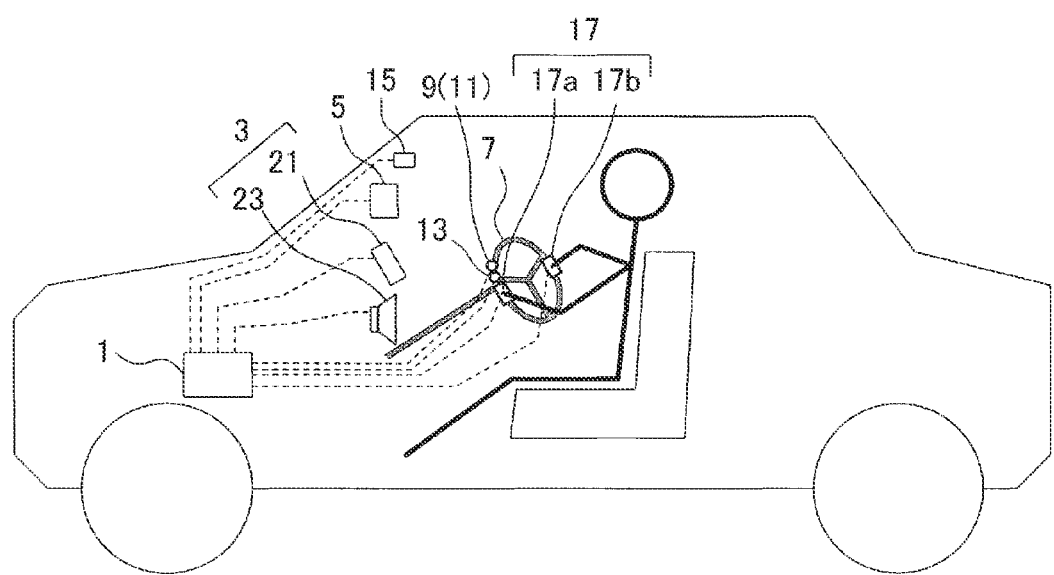
FIG. 1 is an explanatory view illustrating a general configuration of a blood pressure estimation system according to a first embodiment of the present invention.

FIG. 1 is an explanatory view illustrating a general configuration of the blood pressure estimation system according to the first embodiment. This blood pressure estimation system functionally includes a pulse wave analyzer according to the present invention.

As shown in FIG. 1, the blood pressure estimation system includes a control unit 1, notification device 3, manual input device 5, pulse wave sensor 9, pressure sensor 11, skin temperature sensor 13, vibration sensor 15 and ECG (electrocardiographic) sensor 17. The notification device 3 notifies the driver, for example, of information. The manual input device 5 enables manual input of data. The pulse wave sensor 9 is attached to a steering wheel 7. The pressure sensor 11 is attached to the rear face of the pulse wave sensor 9. The skin temperature sensor 13 is attached to the steering wheel 7 in addition to the pulse wave sensor 9. The vibration sensor 15 is attached to the inside of the vehicle. The ECG sensor 17 is also attached to the steering wheel 7.

The control unit 1 is an electronic control unit mainly configured by a known microcomputer. The control unit 1 controls the blood pressure estimation system as a whole and performs a blood pressure estimation process, which will be described later, based on the signals derived such as from the pulse wave sensor 9 and the ECG sensor 17.

The notification device 3 is configured by a display 21 and a speaker 23. The display 21 is a liquid crystal display, for example, for displaying information such as of a blood pressure estimated by the control unit 1 and pulse waves acquired by the control unit 1. The speaker 23 outputs contents of the displayed information such as in an audible manner.

The manual input device 5 is an input device, such as a keyboard, a ten-key or a remote controller, which enables a manual input operation for the control unit 1. Alternative to this, the screen of the display 21 may be configured by a touch panel for the input of data.

The pulse wave sensor 9 is an optical sensor provided with a known light-emitting element (LED (light emitting diode)) and a light-receiving element (PD (photodiode)). For example, the pulse wave sensor 9 emits light such as to a finger tip of the driver and uses the reflected wave to detect pulse waves (volume pulse waves). Pulse wave signals used for blood pressure estimation, which will be described later, can be derived from the pulse wave sensor 9.

The pressure sensor 11 detects a pressure applied to the pulse wave sensor 9 (i.e. holding strength applied to the steering wheel 7 at the position of the pulse wave sensor 9) and outputs a signal corresponding to the applied pressure.

The skin temperature sensor 13 detects a temperature of the hand holding the steering wheel 7 and outputs a signal corresponding to the temperature. Alternative to the skin temperature sensor 13, a temperature sensor for measuring the temperature in the vehicle cabin may be provided.

The vibration sensor 15 outputs a signal corresponding to the level of vibration of the vehicle.

The ECG sensor 17 consists of electrodes 17a and 17b which are arranged at the left and right portions, respectively, of the steering wheel 7 so as to be in contact with the driver's left and right hands. The electrodes 17a and 17b are used for the application of voltage to obtain ECG signals. ECG signals used for the blood pressure estimation described later can be obtained from the ECG sensor 17.

Figure 2:
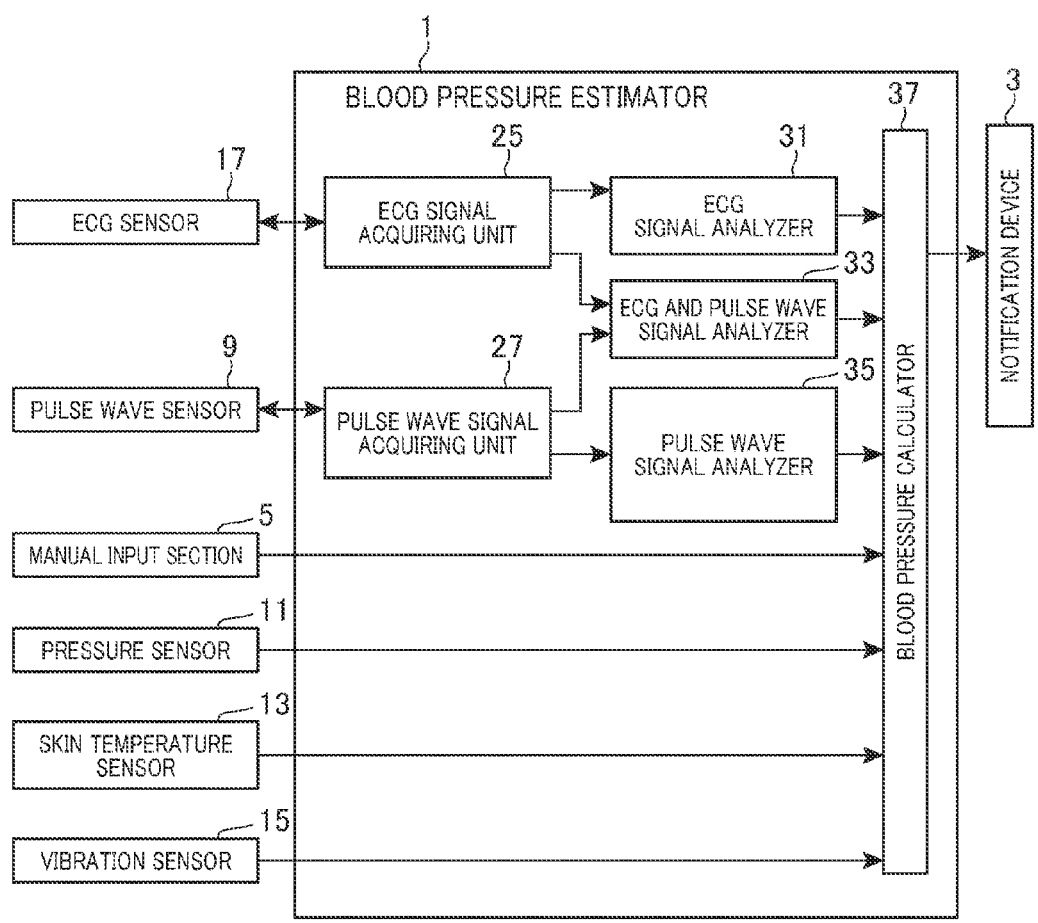
FIG. 2 is a functional block diagram illustrating a control unit in the system.

Referring to FIG. 2, hereinafter is described in detail functions such as of the control unit 1 of the present embodiment. FIG. 2 is a functional block diagram illustrating the control unit 1.

As shown in FIG. 2, the control unit 1 includes an ECG signal acquiring unit 25, pulse wave signal acquiring unit 27, ECG signal analyzer 31, ECG and pulse wave signal analyzer 33, pulse wave signal analyzer 35 and blood pressure calculator 37.

Of these segments, the ECG signal acquiring unit 25 measures an electrical activity accompanying the cardiac activity, in the form of a potential difference (ECG signal) between the electrodes 17a and 17b of the ECG sensor 17.

The pulse wave signal acquiring unit 27 activates the pulse wave sensor 9 and acquires pulse wave signals.

The ECG signal analyzer 31 analyzes ECG signals. Specifically, the ECG signal analyzer 31 filtrates ECG signals acquired by the ECG signal acquiring unit 25, using a low-pass filter (LPF), followed by extracting R-peaks, or calculates a R-R interval (RRI), a heart rate (HR) and the like.

The ECG and pulse wave signal analyzer 33 uses ECG signals and pulse wave signals to calculate a pulse transit time (PTT) that is a delay of a pulse wave signal from an ECG signal (see FIG. 3).

The pulse wave signal analyzer 35 analyzes pulse wave signals to perform single differentiation (velocity pulse waves), double differentiation (acceleration pulse waves), triple differentiation, quadratic differentiation. At the same time, for example, the pulse wave signal analyzer 35 calculates feature points (or feature quantities) (e.g., "a1" to "f1" of the velocity pulse waves and "a" to "f" of the acceleration pulse waves) in each of the differentiations and also calculates AI (volume augmentation index: ratio between progressive wave peaks and reflective wave peaks calculated from volume pulse waves) (see FIG. 4).

The blood pressure calculator 37 estimates (calculates) a blood pressure by a known process using the feature quantities, such as PTT, HR and RRI, obtained from biological information of the pulse wave signals and the ECG signals, feature quantities such as of velocity pulse waves and acceleration pulse waves, and volume AI. As a process of blood pressure estimation, the one disclosed in JP-A-2008-302127 or JP-A 2009-036789 may be used.

The blood pressure calculator 37 performs a process feature of the present embodiment. Specifically, the blood pressure calculator 37 calculates a reference pulse wave and extracts the above feature quantities using the reference pulse wave. A process of calculating the reference pulse wave is described below.

The reference pulse wave of the present embodiment is calculated by averaging pulse wave signal pieces that are obtained by cutting off pulse wave signals on a beat-by-beat basis.

Figure 5:
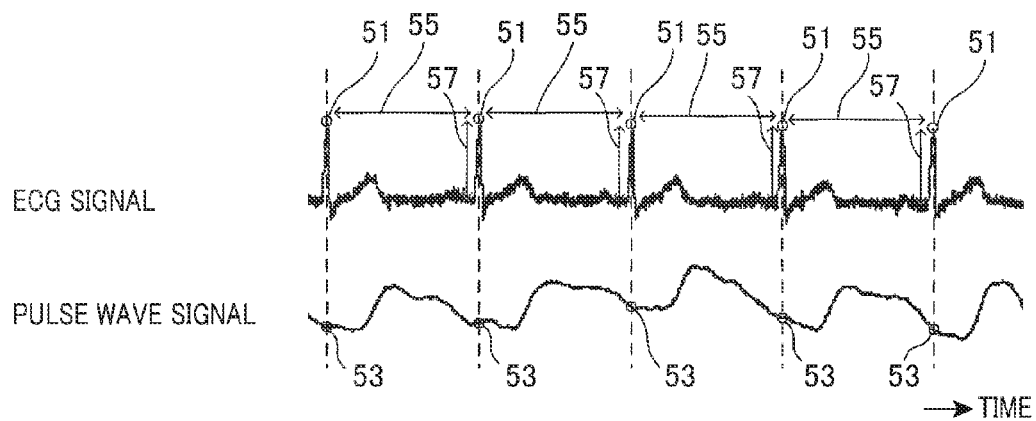
FIG. 5 is an explanatory view illustrating a process of determining base points and a process of determining the accuracy of an ECG signal.

Referring to FIG. 5, cut-off of the pulse waves is described. FIG. 5 is an explanatory view illustrating a process of determining base points and a process of determining the accuracy of an ECG signal. The control unit 1 filtrates ECG signals, which have been acquired at the same time with pulse wave signals, using an LPF (low-pass filter) having a cutoff frequency of 20 Hz. Then, the control unit 1 detects peaks 51 of R-peaks in the waveforms of the ECG signals. A process of detecting the peaks 51 of R-peaks is well known and thus description of the process is omitted. Times when the peaks 51 of R-peaks are detected are set as base points 53 for segmenting the pulse wave signal on a beat-by-beat basis to thereby define pulse wave signal pieces. Then, each portion sandwiched between the base points 53 in the pulse wave signals, is cut off as a separate pulse wave signal.

Referring to FIG. 5, hereinafter is described a process of determining the accuracy of an ECG signal.

The "ECG signal" of which the accuracy is determined here refers to one ECG signal of one heartbeat that corresponds to one separate pulse wave signal of one heartbeat, i.e. refers to a portion sandwiched by the peaks 51 of R-peaks. The accuracy of an ECG signal is determined based on R-peak heights 57 of two R-peaks sandwiching the ECG signal of one heartbeat, and an RRI (R-R interval) 55 of the ECG signal, i.e. the distance between the peaks 51.

Specifically, each of the two R-peak heights 57 and the RRI 55 are compared with respective reference values to determine whether or not differences from the respective reference values are less than predetermined respective thresholds. If the differences are all less than the predetermined thresholds, the ECG signal of one heartbeat is determined as having high accuracy. If any one of the differences is not less than the threshold, the ECG signal is determined as having low accuracy.

It should be appreciated that the "reference values" of the RRI and the R-peak height here may refer to an average value of the RRIs and an average value of R-peak heights acquired in advance from the examinee (driver), or may be average values in these respective items acquired in advance from a plurality of persons. However, the configuration for determining the reference values is not limited to this. The reference values may be determined using various methods.

The control unit 1 cuts off the acquired pulse wave signals using the process described above to obtain pulse wave signal pieces. Of the plurality of cut-off pulse wave signal pieces, those pulse wave signal pieces which correspond to the ECG signals that are determined to have high accuracy are used for the calculation of a reference pulse wave through the averaging of the pulse wave signal pieces.

Figure 6A:
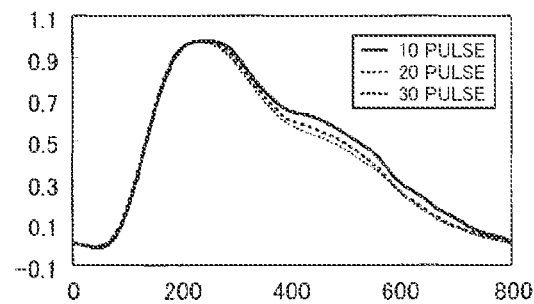
FIG. 6A is a diagram illustrating pulse waveforms used for calculating a reference pulse wave by averaging pulse wave signal pieces which are cut off based on peaks of R-peaks.
Figure 6B:
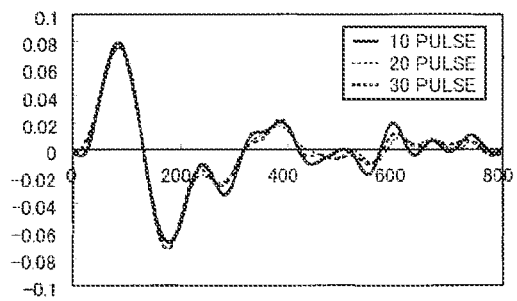
FIG. 6B is a diagram illustrating waveforms of acceleration pulse waves obtained by doubly differentiating the waveforms of FIG. 6A.
Figure 6C:
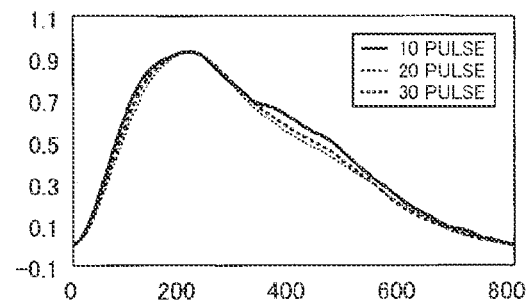
FIG. 6C is a diagram illustrating pulse waveforms obtained by averaging pulse wave signal pieces which are cut off based on rising edges of pulse waves.
Figure 6D:
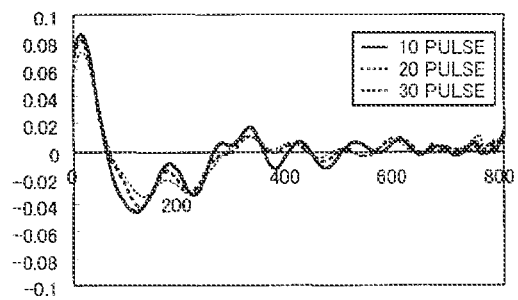
FIG. 6D is a diagram illustrating waveforms of acceleration pulse waves obtained by doubly differentiating the waveforms of FIG. 6C.

FIG. 6A illustrates pulse waveforms used for calculating a reference pulse wave by averaging pulse wave signal pieces which are cut off based on peaks of R-peaks. FIG. 6B illustrates waveforms of acceleration pulse waves obtained by doubly differentiating the waveforms of FIG. 6A. FIG. 6C illustrates, as a comparative example of FIG. 6A, pulse waveforms obtained by averaging pulse wave signal pieces which are cut off based on rising edges of pulse waves. FIG. 6D illustrates, as a comparative example of FIG. 6B, waveforms of acceleration pulse waves obtained by doubly differentiating the waveforms of FIG. 6C. The "rising edge" here refers to a point of minimum value between the peaks of pulse waves. Each of FIGS. 6A, 6B, 6C and 6D shows waveforms obtained by adding the pulse wave signal pieces of 10 heartbeats, 20 heartbeats and 30 heartbeats.

In FIG. 6B, averaging of a number of pulse wave signal pieces causes only small variation in the positions of the peaks and the shapes of the waveforms. Thus, in FIG. 6B, a reference pulse wave of high accuracy is obtained without causing broadening by the averaging of the signals.

On the other hand, in FIG. 6D, the variation in the rising edges of the pulse waves causes deterioration in the accuracy of the base points. Accordingly, the averaging of the signals results in the broadening of the peaks, and the tendency of the broadening is prominent as the number of pulse wave signal pieces to be added is increased. This means that the peaks of the waveforms are not averaged at correct positions and that a time lag is caused. Thus, it will be understood that feature points are varied and that appropriate pulse waveforms cannot be outputted.

Figure 7:
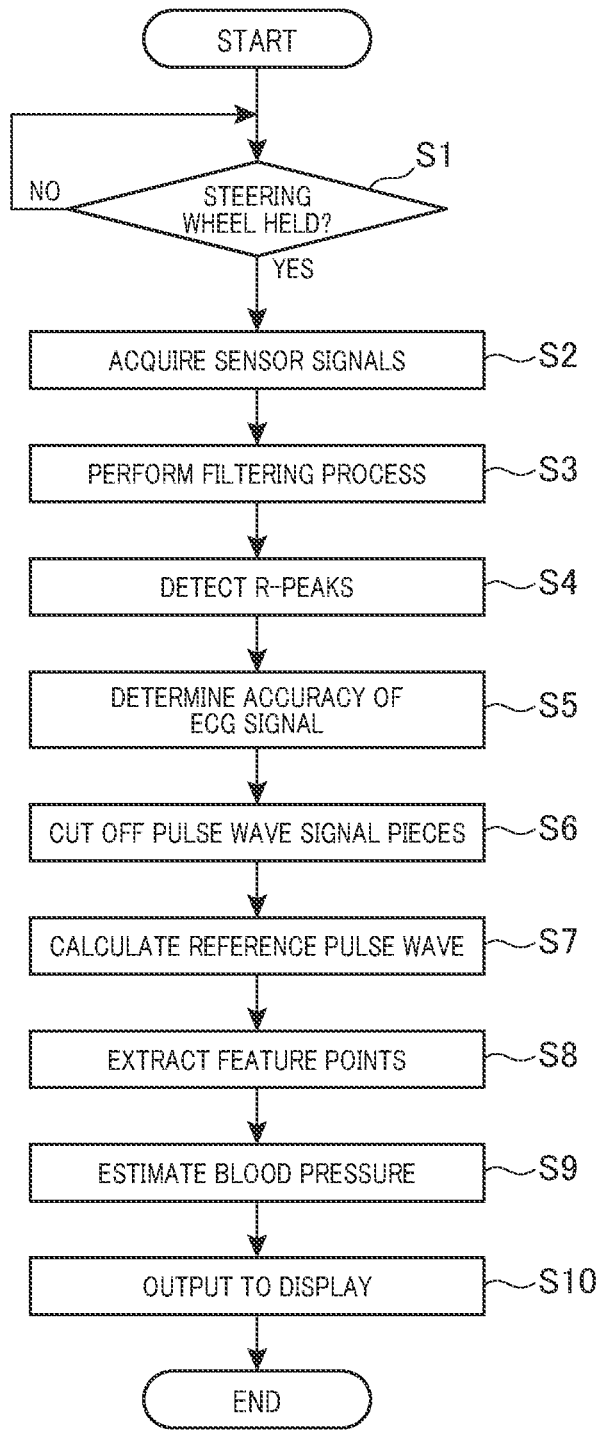
FIG. 7 is a flow diagram illustrating steps of a blood pressure estimation process according to the first embodiment of the present invention.

Referring now to FIG. 7, hereinafter is described a blood pressure estimation process performed by the control unit 1. FIG. 7 is a flow diagram illustrating steps of the blood pressure estimation process. The blood pressure estimation process is started when an input operation for starting the blood pressure estimation process is performed by the manual input section 5.

In the blood pressure estimation process, it is confirmed, first, whether the examinee (driver) holds the steering wheel 7 (step S1). Specifically, at step S1, the steering wheel 7 is determined as being held when ECG signals are detected by the ECG sensor 17. Alternative to this, the steering wheel 7 may be determined as being held based on the output signals such as of the pulse wave sensor 9, the pressure sensor 11 or the skin temperature sensor 13, other than the ECG sensor 17.

If the steering wheel 7 is not held (NO at step S1), control stands by repeating the step of S1 until the steering wheel 7 is held. If the steering wheel 7 is held (YES at step S1), control proceeds to step S2.

Then, pulse wave signals and ECG signals are acquired from the pulse wave sensor 9 and the ECG sensor 17 (step S2). Specifically, at step S2, signals are acquired during a period (e.g., 20 sec) when signals corresponding to a predetermined number of heartbeats or more can be acquired.

Then, the acquired ECG signals are filtrated using an LPF (low-pass filter) having a cutoff frequency of 20 Hz (step S3). After that, R-peaks are extracted from the waveforms of the ECG signals to detect peaks of R-peaks (step S4).

Then, the accuracy of the ECG signals is determined (step S5). Specifically, at step S5, the accuracy of an ECG signal for each heartbeat is determined as described above.

Subsequently, the pulse wave signals acquired at step S2 are delimited using times of the peaks of R-peaks detected at step S4 to cut off pulse wave signal pieces on a beat-by-beat basis (step S6).

Then, a reference pulse wave is calculated (step S7). Specifically, at step S7, of the plurality of pulse wave signal pieces cut off at step S6, only those which are determined, at step S5, to correspond to the ECG signals having high accuracy are selected, followed by averaging the selected pulse wave signal pieces. As a result of the averaging, a reference pulse wave is obtained.

Then, feature points used for blood pressure estimation are extracted from the reference pulse wave (step S8). Specifically, at step S8, the reference pulse wave is doubly differentiated to calculate acceleration pulse waves. Based on the waveforms of the acceleration pulse waves and the ECG signals, feature points (e.g., PTT, RH, AI, acceleration pulse waves "a" to "f", etc.) are extracted.

After that, a blood pressure is estimated based on the feature points extracted at step S8 (step S9). Then, the estimated blood pressure is outputted and displayed on the display 21 (step S10). In displaying the estimated blood pressure, the contents may be outputted from the speaker 23 in an audible manner. After performing step S10, the blood pressure estimation process is terminated.

In the blood pressure estimation system configured as described above, base points for segmenting the pulse wave signal are determined using the feature points (peaks of R-peaks) of ECG signals. Then, based on the base points, pulse wave signal pieces are cut off from the pulse wave signals. Accordingly, the positions of the base points are not varied unlike the case where base points are determined based on pulse wave signals. Also, the influence of noise is unlikely to become large due to differentiation, unlike the case where base points are determined by differentiating pulse wave signals. Thus, a separate pulse wave signal for each heartbeat can be cut off with high accuracy. Accordingly, the pulse wave signal pieces are averaged with high accuracy to thereby calculate a reference pulse wave of high accuracy. In this way, a blood pressure can be estimated with high accuracy.

In the blood pressure estimation system described above, ECG signals are filtrated using a low-pass filter. Owing to the filtration, the influence of high-frequency electromagnetic noise or noise caused by vibration or body motion is mitigated even when the noise is superposed on the ECG signals. Thus, the base points for cutting off pulse wave signals can be determined with good accuracy.

Further, in the blood pressure estimation system described above, a reference pulse wave is calculated by selecting pulse wave signal pieces that correspond to ECG signals having high accuracy. Accordingly, the accuracy of a reference pulse wave is prevented from being deteriorated, which accuracy would otherwise have been deteriorated if pulse wave signal pieces of low accuracy are used.

Second Embodiment

Referring now to FIGS. 8A to 8C, 9 and 10, hereinafter is described a blood pressure estimation system according to a second embodiment of the present invention. The blood pressure estimation system of the second embodiment basically has the same configuration as that of the blood pressure estimation system of the first embodiment. However, in the second embodiment, contents of processes performed in the system are partially changed. In the following description, description is given centering on the changes from the first embodiment, omitting the description of parts similar to those of the first embodiment. Further, the components identical with or similar to those of the first embodiment are given the same reference numerals for the sake of omitting unnecessary explanation.

Hereinafter is described a process of calculating a reference pulse wave in the blood pressure system of the second embodiment. In the second embodiment, every time a new separate pulse wave signal is acquired, the reference pulse wave is updated using the newly acquired separate pulse wave signal as well as the pulse wave signal pieces that have already been acquired. The process of cutting off pulse wave signal pieces is similar to the process of the first embodiment.

Figure 8A:
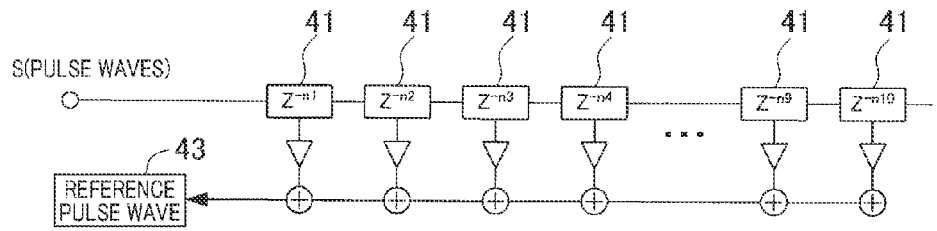
FIGS. 8A to 8C are explanatory views illustrating a process of calculating a reference pulse wave according to a second embodiment of the present invention.
Figure 8B:
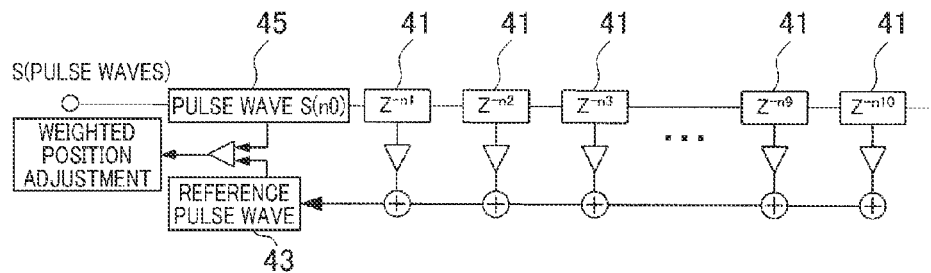
Figure 8C:
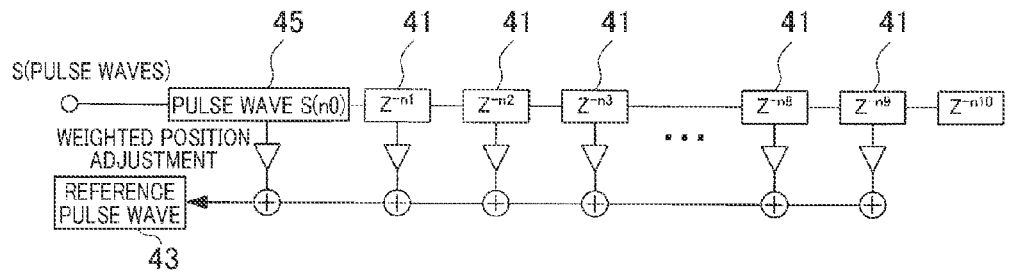
Figure 9:
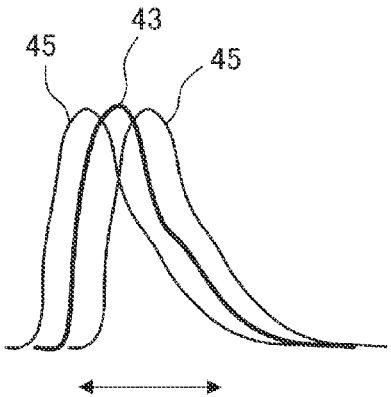
FIG. 9 is an explanatory view illustrating position adjustment of a separate pulse wave signal along a time axis according to the second embodiment.

FIGS. 8A to 8C are diagrams illustrating the process of calculating a reference pulse wave. As shown in FIG. 8A, a reference pulse wave 43 is calculated as a weighted average by weighting each of a plurality of already acquired pulse wave signal pieces 41 and averaging the weighted pulse wave signals 41. In FIG. 8A, the reference pulse wave 43 is calculated using ten pulse wave signal pieces 41, i.e. pulse wave signals $Z^{-n1}$ to $Z^{-n10}$. It should be appreciated that the pulse wave signal $Z^{-n1}$ is the rearmost (newest) data and that the pulse wave $Z^{-n10}$ is the foremost (oldest) data in chronological order.

As shown in FIG. 8B, when a separate pulse wave signal 45 (pulse wave S (n0)) is newly acquired, the position of this separate pulse wave signal 45 is adjusted along a time axis, and at the same time, a weight coefficient is calculated. The reference pulse wave 43 is updated using the calculated weight coefficient and the new separate pulse wave signal 45.

The "position adjustment along a time axis" here refers to shifting the separate pulse wave signal 45 along a time axis (the direction indicated by an arrow in FIG. 9) so as to be well superposed on the reference pulse wave 43 for position adjustment. The process of the position adjustment is specifically described as set forth below at items (A) and (B).

(A) The position of the separate pulse wave signal 45 may be adjusted in respect of a sharpness degree of peaks. In this case, the separate pulse wave signal 45 and the reference pulse wave 43 are averaged to obtain a waveform the pulse waves. The position of the separate pulse wave signal 45 is adjusted along a time axis so that the waveform obtained above will have a predetermined peak with a high sharpness degree. If the position of the separate pulse wave signal 45 is deviated from the reference pulse wave 43, the peak obtained after averaging will be broadened and thus the sharpness degree will be deteriorated. Accordingly, when a high sharpness degree is attained, the position of the separate pulse wave signal 45 may be determined as being appropriate.

A high sharpness degree as mentioned above may be achieved by shifting the position of the separate pulse wave signal 45 little by little. Thus, the position of the separate pulse wave signal 45 may be appropriately adjusted to a position where the sharpness degree of the peak is maximized, or where the sharpness degree of the peak becomes equal to or more than a threshold.

A pulse waveform has a peak of a comparatively low sharpness degree and thus the position may be adjusted based on the sharpness degree of the peak of a velocity pulse wave and an acceleration pulse wave. In calculating the sharpness degree of a peak, the separate pulse wave signal 45 and the reference pulse wave 43 may be differentiated, followed by averaging. Alternatively, in calculating the sharpness degree of a peak, the separate pulse wave signal 45 and the reference pulse wave 43 may first be averaged, followed by differentiation.

The sharpness degree may be calculated from an inclination angle, for example, of a waveform at the time when the height of a peak is reduced to a predetermined height, i.e. at a position apart from the peak by a predetermined time. However, the sharpness degree may be calculated through various processes, without being limited to the processes mentioned above.

(B) The position of the separate pulse wave signal 45 may be adjusted in respect of a correlation coefficient. In this case, the position of the separate pulse wave signal 45 is adjusted along a time axis so that a correlation coefficient between the separate pulse wave signal 45 and the reference pulse wave 43 becomes large. If the position of the separate pulse wave signal 45 is deviated from the reference pulse wave 43, the correlation coefficient between the reference pulse wave 43 and the separate pulse wave signal 45 becomes small. Accordingly, when the correlation coefficient is large, the position of the separate pulse wave signal 45 may be determined as being appropriate.

The correlation coefficient may be calculated by shifting the position of the separate pulse wave signal 45 little by little. Thus, the position of the separate pulse wave signal 45 is adjusted to a position where the correlation coefficient is maximized, or where the correlation coefficient becomes equal to or more than a threshold to thereby obtain an appropriate position of the separate pulse wave signal 45.

When the base points for cutting off pulse wave signal pieces are determined based on ECG signals, an error of about 20 msec is expected to occur at the base points. Accordingly, the sharpness degree or the correlation coefficient may be calculated by adequately shifting the time of the separate pulse wave signal 45 by a time range of ±20 msec (or ±30 msec).

In the present embodiment, each of the ten pulse wave signal pieces is weighted to obtain a weighted average used as a basis for calculating the reference pulse wave 43. As shown in FIG. 8B, when the new separate pulse wave signal 45 is acquired, the control unit 1 calculates a weight coefficient for the separate pulse wave signal 45. Examples of calculating a weight coefficient are specifically explained as set forth below at items (i) to (iii).

(i) A weight coefficient may be calculated by comparing the separate pulse wave signal 45 with the reference pulse wave 43. Specifically, a correlation coefficient between the reference pulse wave 43 and the separate pulse wave signal 45 is calculated. Then, a weight coefficient is determined so that a larger correlation coefficient will allow the separate pulse wave signal 45 to make a larger contribution to the reference pulse wave 43.

As described above, a correlation coefficient is calculated after adjusting the position of the separate pulse wave signal 45 along a time axis.

(ii) A weight coefficient may be calculated based on the accuracy of an ECG signal. The "ECG signal" here refers to an ECG signal of one heartbeat that corresponds to a separate pulse wave signal of one heartbeat. Specifically, the "ECG signal" refers to each portion sandwiched between the peaks 51 of R-peaks. The accuracy of an ECG signal is determined based on two R-peak heights 57 that sandwich the one heartbeat, and the distance between the peaks 51, i.e. the RRI (R-R interval) 55 of the ECG signal. Then, a weight coefficient of the separate pulse wave signal 45 corresponding to the ECG signal of the one heartbeat is determined based on the value of the accuracy.

Specifically, the R-peak heights and the RRI in an acquired ECG signal are compared with reference values to calculate an error $\epsilon_1$ of the peak heights and an error $\epsilon_2$ of the RRI. Then, the errors $\epsilon_1$ of the two R-peaks sandwiching the ECG signal of one heartbeat and the error $\epsilon_2$ are each multiplied with a predetermined coefficient, followed by addition of the multiplied values. A value resulting from this calculation is used as an error parameter $\epsilon$ of the ECG signal of the one heartbeat. Then, a weight coefficient is determined so that a smaller error parameter $\epsilon$ will allow the separate pulse wave signal 45 to make a larger contribution to the reference pulse wave 43.

It should be appreciated that the reference values of the RRI and the R-peak height here may be an average value of RRIs and an average value of R-peak heights acquired in advance from the examinee (driver), or may be average values in these respective items acquired in advance from a plurality of persons. However, the configuration for determining the reference values is not limited to this. The reference values may be determined using various methods.

In the present embodiment, the accuracy of an ECG signal is also used in selecting a separate pulse wave signal (step S26 of FIG. 10 described later).

(iii) A weight coefficient may be calculated based on a signal derived from a sensor that measures disturbance. Specifically, a weight coefficient may be determined so that a smaller disturbance at the timing of acquiring a pulse wave signal will allow the separate pulse signal 45 to make a larger contribution to the reference pulse waves 43. The "disturbance" here refers to a disturbance that prevents normal detection of ECG signals or pulse wave signals.

For example, the disturbance may be vibration, low temperature, and contact failure between the pulse wave sensor 9 and the examinee (driver). When the control unit 1 and the examinee (driver) are vibrated, such as when the vehicle is started, the outputted pulse wave signals and the ECG signals tend to be mixed with noise. Under low-temperature conditions, for example, the blood flow volume in the skin surface is reduced and thus the amplitude of the pulse wave signals is reduced. As a result, noise components are relatively increased and thus pulse waves are unlikely to be accurately measured. The information on disturbance can be acquired using, for example, the pressure sensor 11, the skin temperature sensor 13 and the vibration sensor 15.

As described above, a weight coefficient may be calculated using one of the processes of items (i) to (iii) set forth above, or using a couple of the processes in combination.

As shown in FIG. 8C, after calculating a weight coefficient, the total of ten pulse wave signals, i.e. the separate pulse wave signal 45 and the pulse wave signals $Z^{-n1}$ to $Z^{-n9}$, are each weighted using the weight coefficient and averaged to update the reference pulse wave 43. The pulse wave $Z^{-n10}$ that is the foremost (oldest) data in chronological order is replaced by the separate pulse wave signal 45 and is no longer used.

Figure 10:
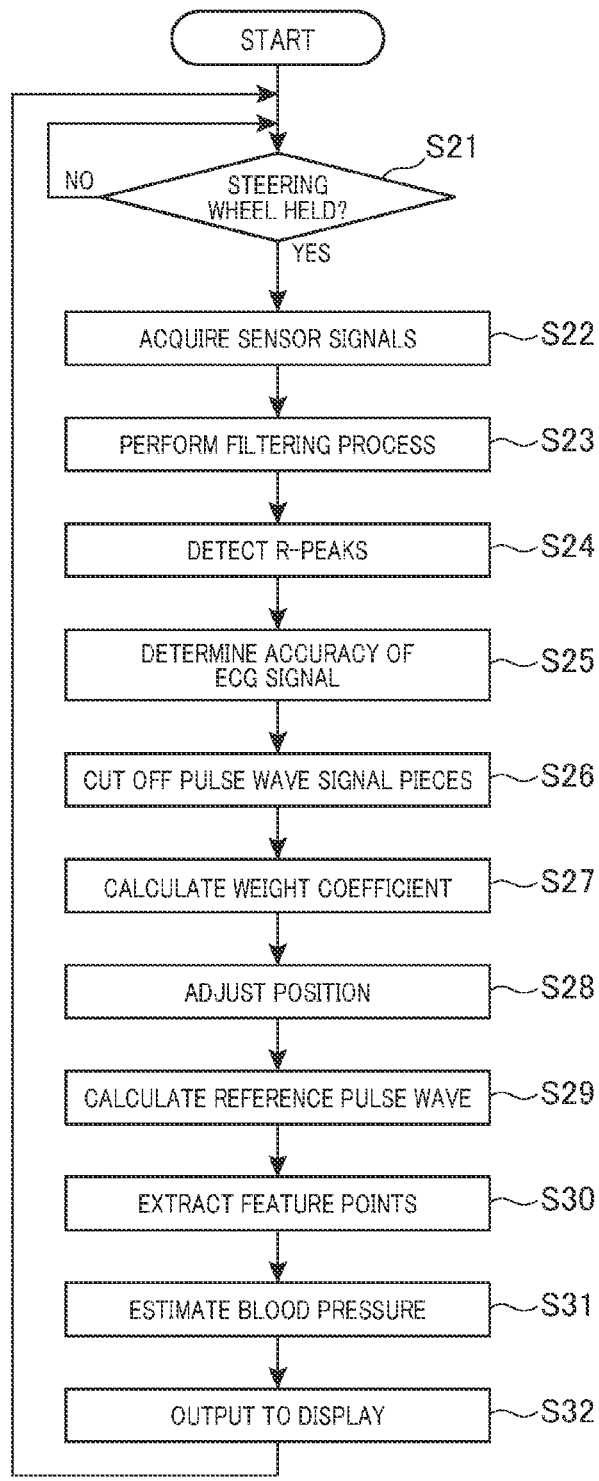
FIG. 10 is a flow diagram illustrating steps of a blood pressure estimation process according to the second embodiment of the present invention.

Referring to FIG. 10, hereinafter is described a blood pressure estimation process performed by the control unit 1 of the present embodiment. FIG. 10 is a flow diagram illustrating steps of the blood pressure estimation process according to the present embodiment. The blood pressure estimation process is started when the control unit 1 is activated with the startup of the vehicle and repeatedly performed during the activation.

In the blood pressure estimation process, it is confirmed, first, whether the examinee (driver) holds the steering wheel 7 (step S21). This step is similar to step S1 of FIG. 7.

Then, pulse wave signals and ECG signals are acquired from the pulse wave sensor 9 and the ECG sensor 17, respectively (step S22). Specifically, at step S22, these signals are acquired during a period (e.g., 10 sec) in which not less than a predetermined number of heartbeats can be confirmed.

At steps S23 and S24, the ECG signals are filtrated using an LPF and then peaks of R-peaks are detected. These steps are similar to steps S3 and S4, respectively, of FIG. 7.

Then, the accuracy of each ECG signal is detected (step S25). Specifically, at step S25, the accuracy of an ECG signal is detected using the process described at the above item (ii).

Then, the pulse wave signals acquired at step S22 are delimited using times of the peaks detected at step S24 as base points, followed by cutting off pulse wave signal pieces on a beat-by-beat basis (step S26). Further, at step S26, of the plurality of cut-off pulse wave signal pieces, one separate pulse wave signal is selected, which corresponds to an ECG signal detected at step S25 having the highest accuracy (i.e. having the smallest error parameter $\epsilon$).

Then, a weight coefficient is calculated (step S27). The weight coefficient is calculated using any one of the processes described at the above items (i) to (iii). The calculation of a weight coefficient may be conducted using any one of the processes or using two or more processes in combination.

Subsequently, the selected separate pulse wave signal is positionally adjusted along a time axis (step S28). Specifically, at step S28, the position adjustment is conducted using either one of the processes explained at the above items (A) and (B).

Then, a reference pulse wave is calculated (step S29). Specifically, at step S29, a reference pulse wave is calculated based on the separate pulse wave signal cut off at step S26 and positionally adjusted at step S28 of the currently running loop, as well as nine pulse wave signal pieces of reverse chronological order, which have been cut off at step S26 of the previous and the older loops. Specifically, when a weight coefficient is "$n_i$" for ten pulse wave signal pieces "$X_i$", a reference pulse wave is calculated from the following formula:

$$(X_1 n_1 + \ldots + X_{10} n_{10})/(n_1 + \ldots + n_{10})$$

where "$X_i n_i$" is a product of the two variables "$X_i$" and "$n_i$".

Soon after the start of the present blood pressure estimation process, when step S26 has not yet been performed for nine times, the shortage of the pulse wave signal pieces is covered by preset initial pulse wave signal pieces. Specifically, at step S29 of the loop run for the first time in the blood pressure estimation process, a reference pulse wave is calculated using nine initial pulse wave signal pieces and the pulse wave signal cut off at step S26 of the currently running loop. Every time a loop of steps of S21 to S32 is completed, the number of initial pulse wave signal pieces to be used is decremented. When the process of item (i) is used at step S27 as well, initial pulse wave signal pieces may be used soon after the start of the blood pressure estimation process.

The initial pulse wave signal pieces may be given general-purpose pulse wave signal pieces, or may be values that have been measured in advance from the examinee such as before the vehicle starts traveling. Multiple initial pulse wave signal pieces may be prepared being correlated to heart rates. When such multiple initial pulse wave signal pieces are used for the blood pressure estimation process described above, the initial separate pulse wave signal corresponding to the heart rate of the moment may be selected and used.

The subsequent steps S30 to S32 are similar to steps S8 to S10, respectively, of FIG. 7. When step S32 has been completed, control returns to step S21.

In the pulse wave estimation system configured as described above, a newest reference pulse wave can be consecutively acquired based on a newly acquired separate pulse wave signal.

When a separate pulse wave signal is newly acquired, a correlation coefficient between the newly acquired separate pulse wave signal and an already calculated reference pulse wave is calculated, or a sharpness degree of a predetermined peak of a waveform is calculated, the waveform being based on the already calculated reference pulse wave and an averaged pulse wave. The calculated correlation coefficient or the sharpness degree is used as a basis for adjusting the position of the newly acquired separate pulse wave signal along a time axis, and then, a reference pulse wave is calculated based on this positionally adjusted separate pulse wave signal and other pulse wave signal pieces.

Thus, the averaging of the newly acquired separate pulse wave signal and other pulse wave signal pieces is suppressed from being conducted at a position where the waveforms of these signals are deviated from each other. Accordingly, the waveform of the reference pulse wave is suppressed from being broadened.

In the pulse wave estimation system described above, each of pulse wave signal pieces is weighted with a weight coefficient based on the measurement accuracy of a separate pulse wave signal, for the averaging of the pulse wave signal pieces. Accordingly, a reference pulse wave can be calculated with high accuracy.

[Modifications]

Some embodiments of the present invention have been described so far. However, the present invention is not limited to the embodiments described above but may, as a matter of course, be variously modified as far as the modifications fall within the technical scope of the present invention.

For example, the second embodiment exemplifies the case where a correlation coefficient between a separate pulse wave signal and a reference pulse wave is calculated to determine a weight coefficient. However, when the correlation coefficient is less than a predetermined threshold, the separate pulse wave signal of the moment may not be used for the calculation of a reference waveform. The threshold in this case may be set such as to 0.7. The ground for this setting is explained using FIGS. 11A to 11D and 12.

FIGS. 11A to 11D are graphs in each of which averaged waveforms resulting from double differentiation of the ten pulse wave signal pieces (hereinafter referred to as "averaged double differential waveforms") are indicated together with reference pulse waves (both of them are acceleration pulse waves). An average value M is different between the graphs of FIGS. 11A to 11D. The average value M is an average of the correlation coefficients between the pulse wave signal pieces that are the bases of the averaged double differential waveforms, and the respective reference pulse waves. The reference pulse waves may be interpreted as waves obtained by measuring pulse wave signal pieces under undisturbed conditions.

Figure 11A:
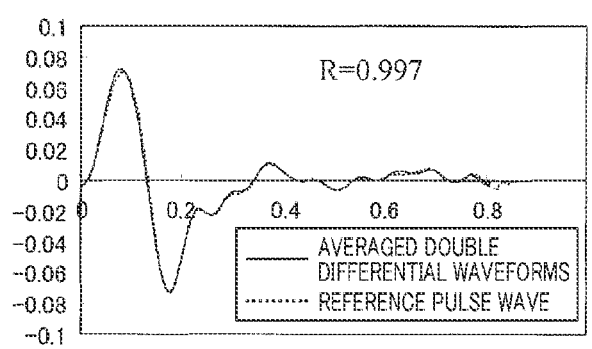
FIGS. 11A to 11D are graphs explaining a process of determining a threshold according to a modification of the invention.

FIG. 11A is a graph in which the average value M is 0.933. Similarly, the average value M is 0.775 in FIG. 11B, 0.750 in FIG. 11C and 0.586 in FIG. 11D.

Figure 11B:
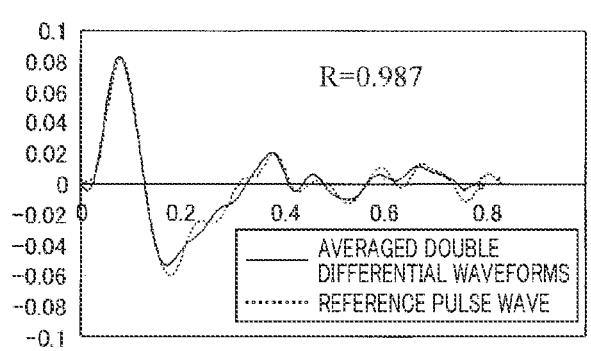
Figure 11C:
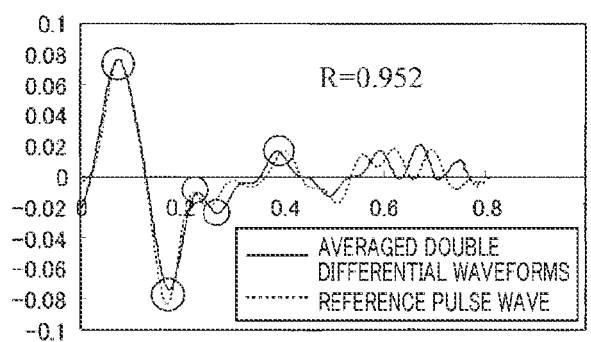
Figure 11D:
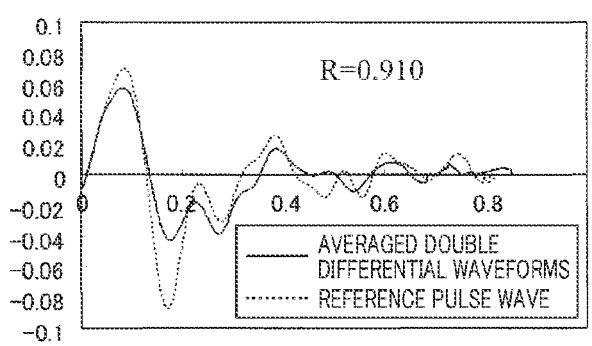

A correlation coefficient R between the averaged double differential waveforms and the reference pulse waves is 0.997 in FIG. 11A, 0.987 in FIG. 11B, 0.952 in FIG. 11C and 0.910 in FIG. 11D. Visually reviewing whether or not the averaged double differential waveforms indicate correct peaks, it is understood that peaks are detected substantially synchronizing with the reference pulse waves when the correlation coefficient R is 0.95 or more, as shown in FIG. 11C.

Figure 12:
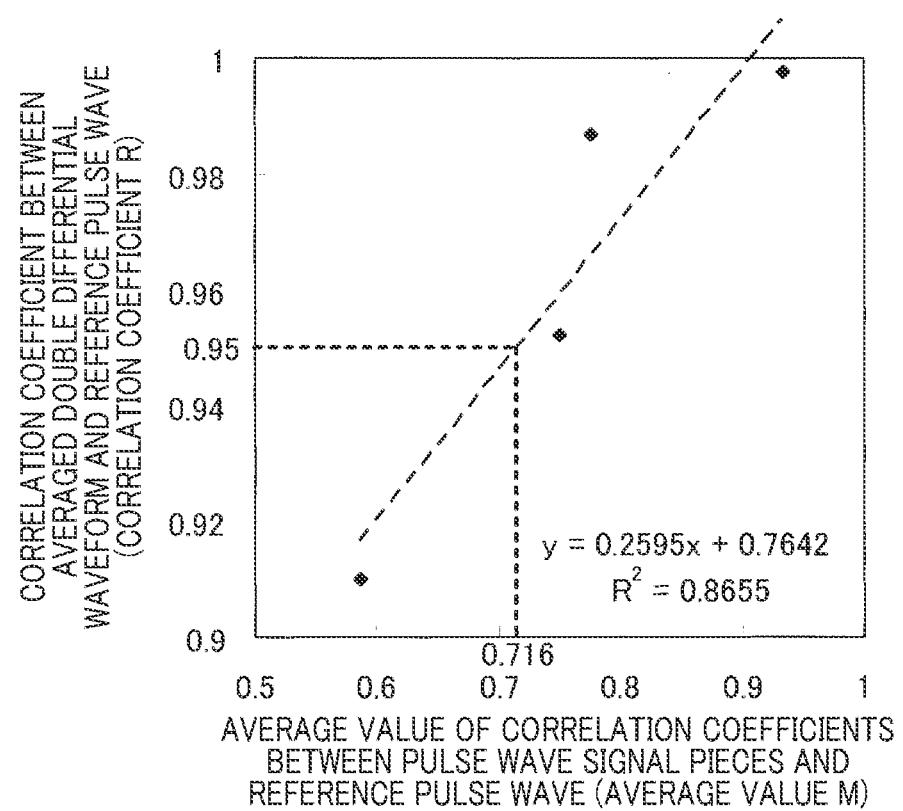
FIG. 12 is a graph explaining a process of determining the threshold according to the modification.

FIG. 12 is a graph plotted with the correlation coefficients R and the average values M of FIGS. 11A to 11D. The vertical axis indicates the correlation coefficient R (correlation coefficient between averaged double differential waveforms and reference pulse waves), and the horizontal axis indicates the average value M (average value of the correlation coefficients between pulse wave signal pieces and reference pulse waves). In the graph, references (A) to (D) are assigned to plots of FIGS. 11A to 11D, respectively.

As described above, when the correlation coefficient R is about 0.95 or more, deviation of the peaks in the double differential waveforms is small. Accordingly, there is no problem if the averaged double differential waveforms are analyzed as being based on correct pulse waves. As will be understood from the graph of FIG. 12, the correlation coefficient R is small when the averaged double differential waveforms are calculated based on pulse wave signal pieces having low correlation with reference pulse waves.

Therefore, in order to render the correlation coefficient R to be a predetermined value or more, the average double differential waveforms may be created using pulse wave signal pieces having a correlation coefficient of a certain threshold or more for the reference pulse waves. The threshold depends on pulse wave signal pieces and thus extends over a certain range. Therefore, such a threshold cannot be univocally determined, but may be estimated by drawing an approximate curve in a graph.

As a result of drawing an approximate line through plots, it will be understood that the average value M is required to be about 0.716 in order to satisfy the correlation coefficient R of 0.95 or more. As mentioned above, taking into account that the value 0.716 is not an exact value, the threshold may be determined to be 0.7. In other words, setting the threshold to 0.7 or more, average double differential waveforms of high accuracy can be obtained.

Accordingly, the calculation of a reference pulse wave in the second embodiment described above may be carried out using pulse wave signal pieces having a correlation coefficient of 0.7 or more between pulse wave signal pieces and reference pulse wave. Thus, data to be removed may be reduced and an accurate reference pulse wave may be obtained.

In the present embodiment, approximately 800 points are sampled for a pulse wave of one heartbeat and a correlation is provided using the data of the approximately 800 points.

Also, the embodiments described above exemplify that ECG signals are filtrated using a low-pass filter having a cutoff frequency of 20 Hz. However, if only the cutoff frequency falls within a range of 15 Hz to 30 Hz, noise may be well removed. It should be appreciated that the cutoff frequency of a low-pass filter may be changed in accordance with disturbance. For example, the cutoff frequency may be set to 20 Hz when the vibration level detected by the vibration sensor 15 is not less than a predetermined threshold, or may be set to 30 Hz when the vibration level is not more than the threshold. Alternatively, ECG signals may not be filtrated by a low-pass filter.

In the second embodiment described above, one separate pulse wave signal is selected and cut off, at step S26, from among the pulse wave signals acquired at step S22 to use the separate pulse wave signal for the update of the reference pulse wave. Alternative to this, the reference pulse wave may be updated at every acquisition of a separate pulse wave from among all the pulse wave signal pieces included in the acquired pulse wave signals.

The second embodiment described above exemplifies that a separate pulse wave signal is positionally adjusted along a time axis. In this case, a weight coefficient may be corrected in accordance with the amount of the position adjustment. For example, a separate pulse wave signal whose amount of position adjustment is large may provide a small weight coefficient, and one whose amount of position adjustment is small may provide a large weight coefficient.

In the foregoing embodiments and modifications, various other advantages can be obtained as follows.

When the measurement accuracy of ECG signals is low, the accuracy will also be low in cutting off separate pulse wave signals based on the feature points of the ECG signals. When ECG signals, per se, have disturbance or irregularity due to biological abnormality of the examinee, the pulse wave signals acquired simultaneously with the ECG signals may have a high probability of having errors.

In this regard, with the pulse wave analyzer configured as set forth above, the accuracy of separate pulse wave signals is determined based on the information derived from the ECG signals. Accordingly, in calculating a reference pulse wave, those separate pulse wave signals which are determined to have high accuracy are permitted to make a large contribution and those separate pulse wave signals which are determined to have low accuracy are permitted to make a small contribution. As a result, a reference pulse wave of high accuracy is obtained.

It should be appreciated that the "reference values" here may refer such as to an average value of R-R intervals and an average value of R-peak heights acquired in advance from the examinee, or may be average values in these respective items acquired in advance from a plurality of persons.

In an example, disturbance, if any, may affect the measurement accuracy of pulse wave signals and ECG signals. In this regard, the pulse wave analyzer configured as set forth above is able to reduce the contribution of separate pulse wave signals to a reference pulse wave when the disturbance is determined as heavily affecting the accuracy of the pulse waves. Thus, a reference pulse wave is calculated with high accuracy.

The "disturbance" mentioned above may refer such as to vibration, temperature and a state of contact between a sensor and the examinee.

In the pulse wave analyzer configured as set forth above, a correlation coefficient between a newly acquired separate pulse wave signal and already calculated reference pulse wave is calculated. Thus, a degree of difference between the newly acquired separate pulse wave signal and a reference pulse wave is calculated. A reference pulse wave, which is calculated based on a plurality of separate pulse wave signals, has high reliability compared to the newly acquired separate pulse wave signal. Accordingly, when the degree of difference from the reference pulse signal is large, the new separate pulse wave signal has a high probability of having low measurement accuracy.

Thus, with the pulse wave analyzer configured as set forth above, the contribution of a separate pulse wave signal to a reference pulse wave can be made small when the separate pulse wave signal is determined as having low measurement accuracy. Thus, a reference pulse wave is calculated with high accuracy.

The waveform of a separate pulse wave signal may be analogous to the waveform of a reference pulse wave. However, in this case, the correlation coefficient may be small if the base points calculated from ECG signals are deviated. In this regard, the pulse wave analyzer configured as set forth above is able to correct the deviation of the base points to thereby calculate an appropriate correlation coefficient.

With the pulse wave analyzer configured as set forth above, a newly acquired separate pulse wave signal and the already calculated reference pulse wave are averaged to obtain a waveform of the averaged pulse wave. Then, the deviation of the base points is corrected based on the sharpness degree of a predetermined peak in the obtained waveform to thereby calculate an appropriate correlation coefficient.

Most of the feature points of ECG signals fall within the time range mentioned above. Accordingly, when an adjustment position is searched from within the time range, an appropriate position can almost always be obtained. Also, there is no need of increasing the range of shifting the separate pulse wave signal more than necessary for the calculation of a correlation coefficient. Thus, the processing load of the pulse wave analyzer is mitigated.

When the amount of adjustment in the positions of the base points is large, it may be determined that there is a high probability that the positions of the base points derived from ECG signals and the waveform of the pulse wave signal are different from a reference waveform acquired in advance. In this regard, in the pulse wave analyzer configured as set forth above, a parameter is determined such that a separate pulse wave signal having a smaller amount of adjustment can make a larger contribution. Thus, a pulse wave signal acquired with high accuracy is permitted to make a larger contribution in calculating a reference pulse wave. In this way, a reference pulse wave of high accuracy is calculated.

When the correlation coefficient between the already acquired reference pulse wave and a new separate pulse wave signal is very small, the new separate pulse wave signal has a probability of having very low accuracy. Therefore, a reference pulse wave, when calculated using this new separate pulse wave signal, may have low accuracy.

The pulse wave analyzer configured as set forth above is able to prevent lowering of the accuracy of a reference pulse wave, which would otherwise have been caused by the calculation of a reference pulse wave based on a separate pulse wave signal having low measurement accuracy.

The pulse wave analyzer configured as set forth above is able to calculate a reference pulse wave of the driver or an occupant of the vehicle.

The present invention may be embodied in several other forms without departing from the spirit thereof. The embodiments and modifications described so far are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A pulse wave analyzer comprising:
   signal acquiring means for acquiring an ECG signal and a pulse wave signal which are detected from an object to be analyzed;
   feature point extracting means for extracting a plurality of feature points from the acquired ECG signal, the feature points appearing in a waveform of the acquired ECG signal;
   signal segmenting means for segmenting the acquired pulse wave signal into a plurality of pulse wave signal pieces based on times at which the plurality of feature points appear, each of the pulse wave signal pieces being segmented every heart beat;
   calculating means for calculating, for estimation of a blood pressure of the object, a reference pulse wave based on the plurality of pulse wave signal pieces, by multiplying the plurality of pulse wave signal pieces by coefficients and averaging the plurality of pulse wave signal pieces multiplied by the coefficients, wherein the calculation of the reference pulse wave is performed repeatedly at intervals with a part of the plurality of pulse wave signal pieces interchanged with another new pulse wave signal piece; and
   coefficient setting means for setting the coefficients based on a coefficient of correction between the new pulse wave signal piece and the reference pulse wave calculated immediately before the interchange such that the larger the coefficient of correlation, the larger a contribution of the pulse wave signal pieces to the reference pulse wave.

2. The pulse wave analyzer of claim 1, wherein
   the feature points are peaks of R-peaks of the waveform of the ECG signal.

3. The pulse wave analyzer of claim 2, wherein
   the feature point extracting means includes a low-pass filter whose cutoff frequency is present in a range of 15 to 30 Hz and means for extracting the feature points from the waveform of the ECG signal processed by the low-pass filter.

4. The pulse wave analyzer of claim 3, wherein
   the calculating means comprises adjusting means for adjusting a position of the new pulse wave signal piece in a time axis such that both the new pulse wave signal piece and the reference pulse wave calculated immediately before the interchange have the largest coefficient of correlation therebetween.

5. The pulse wave analyzer of claim 2, wherein the calculating means is configured to adjust a position of the new pulse wave signal piece in a time axis such that both the new pulse wave signal piece and the reference pulse wave calculated immediately before the interchange have the largest coefficient of correlation therebetween.

6. The pulse wave analyzer of claim 1, wherein
   the calculating means comprises adjusting means for adjusting a position of the new pulse wave signal piece in a time axis direction such that both the new pulse wave signal piece and the reference pulse wave calculated immediately before the interchange are averaged to produce a new pulse wave having a waveform having a predetermined peak which presents the largest sharpness degree.

7. The pulse wave analyzer of claim 1, further comprising second coefficient setting means for setting the coefficient based on a parameter showing accuracy of measuring either the pulse signal or the ECG signal such that the higher the accuracy, the larger a contribution of the pulse wave signal pieces to the reference pulse wave.

8. The pulse wave analyzer of claim 7, wherein
the parameter is a quantity based on either a first difference or a second difference, the first difference being between a heat rate interval obtained from the acquired ECG signal and a predetermined reference value thereof, the second difference being between a peak height of R-peaks appearing in the acquired ECG signal and a predetermined reference value thereof, and
the coefficient setting means is configured to set the coefficient such that the smaller either the first difference of the second difference, the larger the contribution.

9. The pulse wave analyzer of claim 7, further comprising disturbance strength acquiring means for acquiring a strength of a disturbance influencing the accuracy,
the quantity is based on the strength of the acquired disturbance, and
the coefficient setting means is configured to set the coefficient such that the weaker the disturbance, the larger the contribution.

10. The pulse wave analyzer of claim 9, wherein
the disturbance strength acquiring means comprises a group of sensors including a vibration sensor, a temperature sensor, and a pressure sensor sensing a pressure between a pulse wave sensor sensing the pulse wave signal and the body, and
the disturbance strength acquiring means is configured to acquire the strength of the disturbance based on signals from one or more sensors selected from the group of sensors.

11. The pulse wave analyzer of claim 7, wherein
the coefficient setting means is configured to calculate the reference pulse wave repeatedly at intervals with a part of the plurality of pulse wave signal pieces interchanged with another new pulse wave signal piece,
the parameter is a quantity based on a coefficient of correlation between the new pulse wave signal piece and the reference pulse wave calculated immediately before the interchange, and
the coefficient setting means is configured to calculate the coefficient such that the larger the coefficient of the correlation, the large the contribution.

12. The pulse wave analyzer of claim 11, wherein
the coefficient setting means is configured to positionally adjust the new pulse wave signal piece in a time axis such that both the new pulse wave signal piece and the reference pulse wave calculated immediately before the interchange have the largest coefficient of correlation therebetween, and
the quantity is based on the coefficient of correlation obtained when the new wave pulse signal piece is positionally adjusted in the time axis.

13. The pulse wave analyzer of claim 11, wherein
the coefficient setting means is configured to positionally adjust the new pulse wave signal piece in a time axis the new pulse wave signal piece and the reference pulse wave calculated immediately before the interchange are averaged to produce a new pulse wave having a waveform having a predetermined peak which presents the largest sharpness degree, and
the quantity is based on the coefficient of correlation obtained when the new wave pulse signal piece is positionally adjusted in the time axis.

14. The pulse wave analyzer of claim 12, wherein
the coefficient setting means is configured to positionally adjust the new pulse wave signal piece in the time axis through an interval of time of .+−.30 msec.

15. The pulse wave analyzer of claim 12, wherein
the coefficient setting means is configure to set the coefficient of the correlation such that the smaller an amount of adjustment of the new pulse wave signal piece in the time axis, the larger the contribution.

16. The pulse wave analyzer of claim 1, wherein
the calculating means is configured to calculate the reference pulse wave repeatedly at intervals with a part of the plurality of pulse wave signal pieces interchanged with another new pulse wave signal piece, check if a coefficient of correlation between the new pulse wave signal piece and the reference pulse wave immediately before the interchange is less than 0.7, and exclude the new pulse wave signal piece from calculating the reference pulse wave if it is checked that the coefficient of the correlation is less than 0.7.

17. The pulse wave analyzer of claim 1, wherein
the pulse wave analyzer is mounted in a vehicle and the object is a crew in the vehicle.

18. The pulse wave analyzer of claim 1, wherein the calculating means is configured to adjust a position of the new pulse wave signal piece in a time axis such that both the new pulse wave signal piece in the reference pulse wave calculated immediately before the interchange have the largest coefficient of correlation therebetween.

19. A method of analyzing a pulse wave, comprising steps of:
acquiring an ECG signal and a pulse wave signal which are detected from an object to be analyzed;
extracting a plurality of feature points from the acquired ECG signal, the feature points appearing in a waveform of the acquired ECG signal;
segmenting the acquired pulse wave signal into a plurality of pulse wave signal pieces based on times at which the plurality of feature points appear, each of the pulse wave signal pieces being segmented every heart beat; and
calculating a reference pulse wave based on the plurality of pulse wave signal pieces, by multiplying the plurality of pulse wave signal pieces by coefficients and averaging the plurality of pulse wave signal pieces multiplied by the coefficients,
wherein the calculation of the reference pulse wave is performed repeatedly at intervals with a part of the plurality of pulse wave signal pieces interchanged with another new pulse wave signal piece.

* * * * *